US009638741B2

United States Patent
Boeykens et al.

(10) Patent No.: US 9,638,741 B2
(45) Date of Patent: May 2, 2017

(54) METHOD AND APPARATUS FOR INSPECTION OF LIGHT EMITTING SEMICONDUCTOR DEVICES USING PHOTOLUMINESCENCE IMAGING

(75) Inventors: Steven Boeykens, Heverlee (BE); Tom Marivoet, Erps-Kwerps (BE)

(73) Assignee: KLA-Tencor Corporation, Milpitas, CA (US)

( * ) Notice: Subject to any disclaimer, the term of this patent is extended or adjusted under 35 U.S.C. 154(b) by 688 days.

(21) Appl. No.: 13/577,518

(22) PCT Filed: Jun. 18, 2012

(86) PCT No.: PCT/IB2012/053052
§ 371 (c)(1),
(2), (4) Date: Aug. 7, 2012

(87) PCT Pub. No.: WO2012/176106
PCT Pub. Date: Dec. 27, 2012

(65) Prior Publication Data
US 2013/0027543 A1 Jan. 31, 2013

Related U.S. Application Data

(60) Provisional application No. 61/500,987, filed on Jun. 24, 2011.

(51) Int. Cl.
*G01R 31/265* (2006.01)
*G01N 21/64* (2006.01)
(Continued)

(52) U.S. Cl.
CPC ..... *G01R 31/2635* (2013.01); *G01N 21/6489* (2013.01); *G01R 31/2656* (2013.01); *H01L 33/0095* (2013.01)

(58) Field of Classification Search
CPC ........... G01N 21/9501; G01N 21/8806; G01N 2021/8861; G01N 21/956; G01N 21/6489;
(Continued)

(56) References Cited

U.S. PATENT DOCUMENTS

| 5,440,384 | A | 8/1995 | Yamada et al. |
| 7,504,642 | B2 | 3/2009 | Hummel et al. |

(Continued)

FOREIGN PATENT DOCUMENTS

| JP | S5857764 A | 4/1983 |
| JP | S6292487 A | 4/1987 |

(Continued)

*Primary Examiner* — Michael Teitelbaum
(74) *Attorney, Agent, or Firm* — Suiter Swantz pc llo (57) ABSTRACT

A method and apparatus for the inspection of light emitting semiconductor devices. The semiconductor device is illuminated with a light source, wherein at least an area of the light emitting semiconductor is illuminated with a waveband of light. The waveband of light $\lambda A + \lambda B$ can generate electron-hole pairs in the light emitting semiconductor to be inspected. Through an objective lens at least a part of the light $\lambda C$ emitted by the light emitting semiconductor is detected. The emitted light is captured with a sensor of a camera that is sensitive to wavelengths of the emitted light, wherein the wavelength of the emitted light is above the width of the waveband. The data of the emitted light, captured with the sensor, are transmitted to a computer system for calculating inspection results of the light emitting semiconductor.

13 Claims, 5 Drawing Sheets (51) Int. Cl.
*H01L 33/00* (2010.01)
*G01R 31/26* (2014.01)

(58) Field of Classification Search
CPC .......... H01L 22/12; G06T 2207/30148; G01R 31/2635
See application file for complete search history.

(56) References Cited

U.S. PATENT DOCUMENTS

| | | | |
|---|---|---|---|
| 2004/0097160 A1* | 5/2004 | Kaltenbach | H01L 51/56 445/3 |
| 2004/0106217 A1* | 6/2004 | Higgs | 438/5 |
| 2004/0207836 A1* | 10/2004 | Chhibber et al. | 356/237.4 |
| 2009/0136120 A1 | 5/2009 | Onushkin et al. | |
| 2010/0067756 A1 | 3/2010 | Hart et al. | |
| 2011/0025839 A1* | 2/2011 | Trupke et al. | 348/87 |

FOREIGN PATENT DOCUMENTS

| | | |
|---|---|---|
| JP | H0697508 A | 4/1994 |
| JP | 10-149705 A | 6/1998 |
| JP | 2005061929 A | 3/2005 |
| JP | 2010-107254 A | 5/2010 |
| WO | 98/11425 A1 | 3/1998 |
| WO | 2007/128060 A1 | 11/2007 |

* cited by examiner

| Material | Bandgap energy [eV] | Wavelength [nm] |
|---|---|---|
| GaN | 3.45 | 359 |
| InN | 0.8 | 1550 |
| $In_{0.26}Ga_{0.74}N$ (blue LED) | 2.75 | 450 |

METHOD AND APPARATUS FOR INSPECTION OF LIGHT EMITTING SEMICONDUCTOR DEVICES USING PHOTOLUMINESCENCE IMAGING

CROSS REFERENCE TO RELATED APPLICATIONS

This patent application claims priority to U.S. provisional patent application No. 61/500,987 filed Jun. 24, 2011, incorporated herein by reference.

FIELD OF THE INVENTION

The present invention relates to a method for inspecting light emitting semiconductor devices during and after a production process. The light emitting semiconductor devices can be LEDs.

The present invention also relates to an apparatus for inspecting light emitting semiconductor devices on a substrate.

BACKGROUND OF THE INVENTION

Solid state lighting (SSL) has several advantages compared to conventional lighting, including low power consumption, long lifetime, and small form factor. An important element of SSL is the LED (Light-Emitting Diode) die/chip. The basis for the LED is a semiconductor material that undergoes a complex production process. Several metrology and inspection steps are done during and after the production process of the LED.

Measuring the output power of an LED is typically done using a probing system. In this system, electrical contact is made with each LED die, and a measurement is done of the generated light output power and, optionally, the wavelength.

The international patent application WO98/11425 discloses a method and apparatus for detecting defects in a semiconductor or silicon structure at room temperature and in an efficient time using photoluminescence. The invention employs the use of a high intensity beam of light, preferably having a spot size between 0.1 mm-0.5 µm and a peak or average power density of $10^4$-$10^9$ W/cm$^2$, to generate a high concentration of charge carriers, which charge characters detect defects in a semiconductor by interacting with same. These defects are visible by producing a photoluminescence image of the semiconductor. Several wavelengths may be selected to identify defects at a selective depth. Additionally, the method uses confocal optics. This method probes a very small volume of the material with one or more laser beams having very small spot size.

Another method is described in U.S. Pat. No. 7,504,642 B2, wherein one or more images are created using filtering and image computation to selectively create a defect image of one selected layer of a wafer, while trying to eliminate unwanted contributions of other layers of the same wafer. The method uses photoluminescence to identify defects in one or more specified material layers of a sample. One or more filtering elements are used to filter out predetermined wavelengths of return light emitted from a sample. The predetermined wavelengths are selected such that only return light emitted from one or more specified material layers of the sample is detected. Additionally or alternatively, the wavelength of incident light directed into the sample may be selected to penetrate the sample to a given depth, or to excite only one or more selected material layers in the sample. Accordingly, defect data characteristic of primarily only the one or more specified material layers is generated.

The international patent application WO 2007/128060 A1 describes a method for testing of indirect bandgap (e.g. Si) semiconductor materials with photoluminescence, based on a comparison of several regions in two or more images. The method is suitable for identifying or determining spatially resolved properties in indirect bandgap semiconductor devices such as solar cells. In one embodiment, spatially resolved properties of an indirect bandgap semiconductor device are determined by externally exciting the indirect bandgap semiconductor device to cause the indirect bandgap semiconductor device to emit luminescence, capturing images of the luminescence emitted from the indirect bandgap semiconductor device in response to the external excitation, and determining the spatially resolved properties of the indirect bandgap semiconductor device based on a comparison of the relative intensities of regions in one or more of the luminescence images.

Quality control of LEDs is becoming more and more crucial since LEDs are used for illumination. For example, it is important that LEDs used for the back illumination of a TV set are of similar intensities. Therefore, quality control of the light output power of LEDs is needed. Previously, such quality control involved electrically contacting the LED (probing) and measuring the emitted light output power. This has several disadvantages: LEDs may get damaged during probing, probing is slow, and probing requires an additional tool.

SUMMARY OF THE INVENTION

It is an object of the invention to provide a method to quickly and reliably measure the light power emitted by an LED during a production process. Furthermore, the method should be easy to use, and should not influence or destroy the LED being measured.

The object is achieved by a method for inspecting light emitting semiconductor devices, comprising the following steps: illuminating with a light source at least an area of a light emitting semiconductor with a waveband of light, wherein the waveband of light $\lambda_A + \lambda_B$ can generate electron-hole pairs in the light emitting semiconductor to be inspected; detecting through an objective lens at least a part of the light $\lambda_C$ emitted by the light emitting semiconductor, wherein the emitted light is captured with a sensor of a camera sensitive to wavelengths of the emitted light and the wavelength of the emitted light is above a width of the waveband; and transferring data of the emitted light, captured with the sensor, to a computer system to calculate the inspection results of the light emitting semiconductor.

It is a further object of the invention to provide an apparatus to inspect the light power emitted by an LED during a production process. Furthermore, the apparatus should be easy to use, and should not influence or destroy the LED being measured.

The object is achieved by an apparatus for inspecting light emitting semiconductor devices on a substrate, comprising: a light source; an objective lens defining a detection beam path; a camera with a sensor positioned in the detection beam path for receiving light from the light emitting semiconductor devices via the objective lens, wherein the sensor registers gray scale values of the light emitting semiconductor devices; a computer system for calculating a wafermap from data registers by the sensor; and a display to visually display the wafermap.

For defect inspection, the photoluminescence effect is used as a kind of back light. This illumination effect enables the finding of defects that are buried, or at least are not visible with normal inspection. With the inventive setup, it is possible to find cuts (finger cuts) or interrupts in the metallization layer. Additionally, the invention allows for the detection of non-homogeneities of the LEDs. The light emitted from the LED is subjected to a spatial gray value analysis. Some LEDs only emit light in some parts, emitting no light in other parts (for example: a dark edge at the corner of the LED does not light up).

According to an embodiment of the invention, the light emitting semiconductor devices are illuminated with a light source configured as a ring light. The ring light has a plurality of LEDs. A second filter may be positioned in the detection beam path. The second filter in the detection beam path prohibits the reflections of the incident light to reach the sensor, but at least a wavelength of $\lambda_C$ passes the second filter.

In a further embodiment of the invention, a first filter is positioned in an illumination beam path of the light source and is designed to pass a waveband $\lambda_A \pm \lambda_B$. A second filter is positioned in a detection beam path, and prohibits the reflections of the incident light to reach the sensor. However, at least a wavelength of $\lambda_C$ passes the second filter. In this case, the objective lens defines the illumination beam path and the detection beam path. The light source is a coaxial light source.

One or several LED die/chips are illuminated by a light source with wavelengths able to generate electron-hole pairs in the LED. The light emitted by the LED (caused by generating the electron-hole pairs and the following recombination process) is captured with a sensor and camera sensitive to the wavelengths of the emitted light. The sensor response (gray value) is a measure of the power of the light output of the LED and can, for example, be used to classify the LEDs according to their light output power.

The waveband of light $\lambda_A \pm \lambda_B$ for the illumination of light emitting semiconductor devices or the LED die/chips is generated by inserting a first filter prior to the objective lens in an illumination beam path. A second filter is positioned in a detection beam path after the objective lens, such that only the light emitted by the light emitting semiconductor reaches the sensor of the camera. The image acquisition setup, especially the objective lens, comprises microscope optics. Various types of illumination can be used in the apparatus for the illumination of light emitting semiconductor devices or the LED die/chips. The light source could be a coaxial light source or a ring light. The illumination light is provided by a plurality of LEDs.

When the inventive method is applied to LED die/chips, which are structures on a substrate or wafer, the inspection results in a measure of the light output power of a LED or the LED die/chips, detected by the sensor of the camera. The output of the sensor is at least one gray value of a matrix of pixels. A range of the gray values establishes a function of the light output power per LED in the LED die/chips or in the light emitting semiconductor devices.

The inventive apparatus has a stage, which moves the substrate with the LED die/chips in a X/Y direction. The movement is controlled by a computer system. With the relative movement between the camera and the substrate, the sensor of the camera can capture an image of the entire surface of the substrate. The data from the sensor is sent to the computer system, which calculates a wafermap of the surface with the LED die/chips. The wafermap is shown on a display of the computer system, wherein each class of gray value is assigned a separate color code.

The function of the light output power per LED is implemented as a look up table. In another embodiment, the function is implemented as a polynomial. A calibration of the look up table or the polynomial is completed by measuring the light output power of an LED sample connected to an electrical prober.

The inspection result generated by the sensor is at least one gray value per LED. The inspection results of the LEDs are sorted in at least two bins according to their registered gray value. Further, the inspection result generated by the sensor is at least two gray values per LED die/chip. The variations or differences in gray value of one LED die/chip are used as a quality measure of the LED die/chip.

The inspection method result includes at least one gray value per LED die/chip comprises the steps of: taking at least two inspection images under the same conditions of each LED die/chip; taking the images under varying illumination intensity and/or exposure settings, wherein the illumination intensity and/or exposure settings are configurable; generating a histogram of the gray values for each LED die; and analyzing the histogram distribution to establish a pass or fail criteria.

The emitted light of the LED die/chips is caused by a recombination process of electron-hole pairs generated by the illumination in an active layer of the LED die/chips. The emitted wavelength or waveband has a similar wavelength or waveband that results when a forward voltage is applied to the LED die/chips.

Due to fluctuations in the production process, the LED die/chips are sorted according to several criteria, including center wavelength of the emitted light, power of the emitted light, etc.

This invention would allow for fast and contactless inspection of light emitting semiconductor devices on an inspection tool widely used by LED manufactures for other inspection tasks.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION OF THE INVENTION

It is noted the same reference numerals refer to the same elements throughout the various figures. Furthermore, only reference numerals necessary for the description of the respective figure are shown in the figures. The shown embodiments represent only examples of how the invention can be carried out and should not be regarded as limiting the invention. The description below refers to LED die/chips, which should not be regarded as limiting the invention. It should be evident for any person skilled in the art that the present invention is applicable to light emitting semiconductor material in general.

Figure 1:
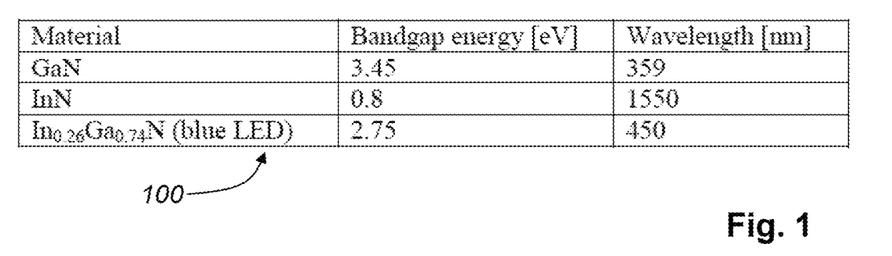
FIG. 1 is a table showing a bandgap and corresponding wavelength of a III-N semiconductor material system.

FIG. 1 is a table 100 showing a bandgap and corresponding wavelength of a III-N semiconductor material system. All semiconductor materials exhibit the so-called photoluminescence effect. This effect is seen when the material is illuminated with light of a certain wavelength and the photons in the light beam raise electrons from a low energy state to a high energy state (generating electron-hole pairs). This process is known as photo-excitation. The incoming light beam should have an energy level above the difference between the high-energy state and the low energy state. This is typically the bandgap energy of the semiconductor material. The generated electron-hole pairs will recombine, and the recombination process will generate photons (radiative recombination) or phonons (non-radiative recombination). In most LED materials (which are direct semiconductors), such as the GaN system, the radiative recombination process is the dominant process.

Figure 2:
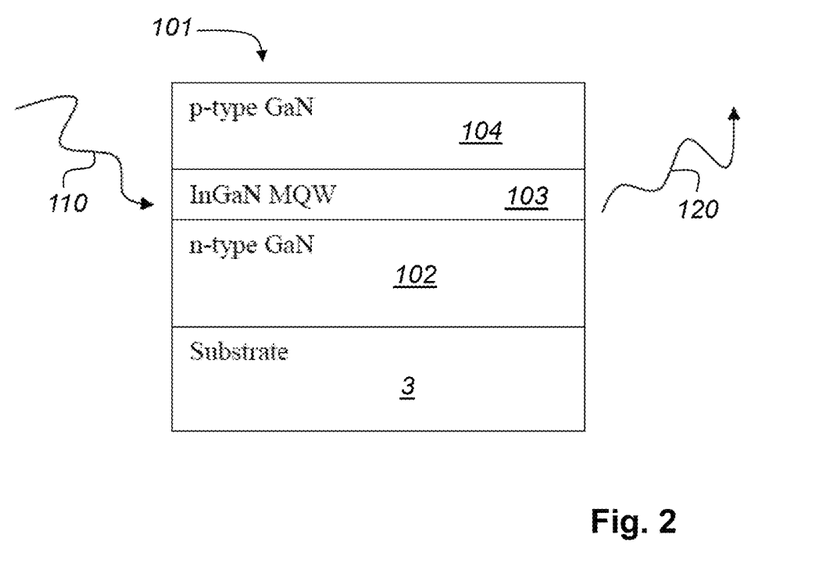
FIG. 2 is a typical layer stack of an LED.

FIG. 2 is a typical representation of a layer stack 101 of an LED. The layer stack 101 has the substrate 3, on which a layer 102 of an n-type GaN is formed. An intermediate layer 103 of an InGaN MQW material is formed on the layer 102 of n-type GaN. A top layer 104 is formed by a p-type GaN material. To probe only the intermediate layer 103 of InGaN MQW, an excitation light 110 should not be absorbed by either the layer 102 of n-type GaN or the top layer 104 of p-type GaN surrounding the layer 103. The excitation light 110 should have an energy level below the GaN energy band level (i.e. a wavelength above 359 nm). For the light to be absorbed by the intermediate layer 103 of InGaN MQW material, the excitation light 110 should have an energy level above 2.75 eV (i.e. below 450 nm). The generated light 120 by the intermediate layer 103 of InGaN MQW material has a wavelength around 450 nm. In the apparatus 1, described in FIG. 3, a white light source 7 is used. Consequently, the energy levels below 450 nm in the light path have to be filtered out through a first low pass filter 15 (pass only wavelengths less than 450 nm). To make clear images not disturbed by the reflections of the incoming light, a second filter 16 is needed in a detection beam path 21 with high-pass characteristics (i.e. pass only wavelengths of 450 nm and higher).

Figure 3:
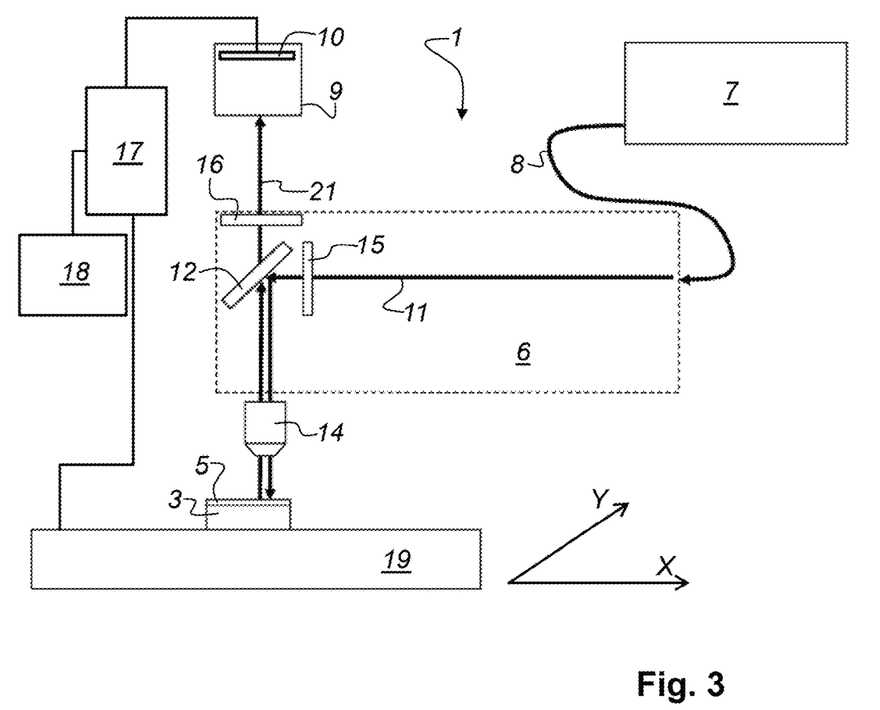
FIG. 3 is an embodiment of an apparatus according to the invention for illuminating one or several LED die/chips and detecting emitted light from the one or several LED die/chips.

FIG. 3 is a schematic representation of an embodiment of the apparatus 1 for illuminating one or several LED die/chips 5 on a substrate 3 to detect the wavelengths of the emitted light from the LED die/chips 5. One or several LED die/chips 5 are illuminated by the light source 7 with wavelengths able to generate electron-hole pairs in the LED die/chips 5. The light emitted by the LED die/chips 5 (caused by generating the electron-hole pairs and the following recombination process) is captured with a camera 9 sensitive to the wavelengths of the emitted light. The camera 9 has a sensor 10, and the response (gray value) of the sensor 10 is a measure of the power of the light output of the LED die/chips 5 and may, for example, be used to classify the LEDs according to their light output power.

The light source 7 is a white-light broadband spectrum light source, and is used for illuminating the substrate 3 with the LED die/chips 5. The light from the light source 7 is supplied to a microscope 6 via a light guide 8. An illumination path 11 is defined by the microscope 6, and is directed by a beam splitter 12 via an objective lens 14 onto the LED die/chips 5 on the substrate 3. By providing a means (not shown) for inserting a respective first filter 15 in the illumination beam path 11, a certain part of the broadband spectrum generated by the light source 7, is selected. The light is transmitted through the objective lens 14 (incident light beam), which excites the semiconductor material in the LED die/chips 5 on the substrate 3. For example, the semiconductor material could be a direct band gap material, such as a III-V semiconductor material used for LED fabrication. The semiconductor material will emit light at a known wavelength, and the light will be collected in the same objective lens 14.

A detection beam path 21 is defined by the objective lens 14. In the detection beam path 21, a second filter 16 is positionable such that only the light emitted by the LED die/chips 5 on the substrate 3 reach the camera 9 and the sensor 10. The second filter 16 prohibits the reflected incident light from reaching the camera 9 or the sensor 10. The image data collected by the sensor 10 of camera 9 is fed to a computer system 17, which uses image processing software to derive an average intensity for each LED on the substrate 3. The computer system 17 computes a wafermap 30 (see FIG. 5). A display 18 of computer system 17 visually displays the wafermap 30, plotting the results of all LEDs and their coordinate position on the substrate 3, (generally a wafer).

The light source 7 is a coaxial light source. It is advantageous if the light source 7 is a ring light source. The illumination light is provided by a plurality of LEDs. The light source 7 is configured as a pulsed light source or a continuous light source. The waveband constraint $(\lambda_A + \lambda_B) < \lambda_C$ is implemented using an optical high pass and/or low pass and/or band pass filters. The sensor 10 is a line sensor. The camera 9 is configured as a TDI (time delay integration) line scan camera. The sensor 10 could be a 2-dimensional sensor, resulting in an area scan camera.

The emitted light of the LED die/chips 5 or LED is caused by the recombination process of electron-hole pairs generated by the illumination, which has a similar wavelength as to what results when a forward voltage is applied to the LED die/chips 5 or LED. The recombination process takes place in the active layer of the LED die/chips 5 or LED. For example, in the case of a blue LED, an example implementation would include the following wavelengths: $\lambda_A \approx 380$ nm, $\lambda_B \approx 20$ nm and $\lambda_C \approx 440$ nm.

A calibration is performed to correlate the measured average intensity of the LED material to an output power (density) number. The inventive apparatus 1 uses a white-light source with area illumination. In contrast, prior art devices use a commonly-known laser beam source with small spot size, and a camera as a detector. The computer system 17 controls an X/Y-stage 19. The X/Y-stage 19 moves the substrate 3 in a controlled manner such that the entire surface of the substrate is imaged by the objective lens 14 onto the sensor 10 of camera 9. The position of the X/Y-stage 19 is recorded to correlate the visually captured data with the position data on the substrate 3 and to generate the wafermap 30.

Figure 4:
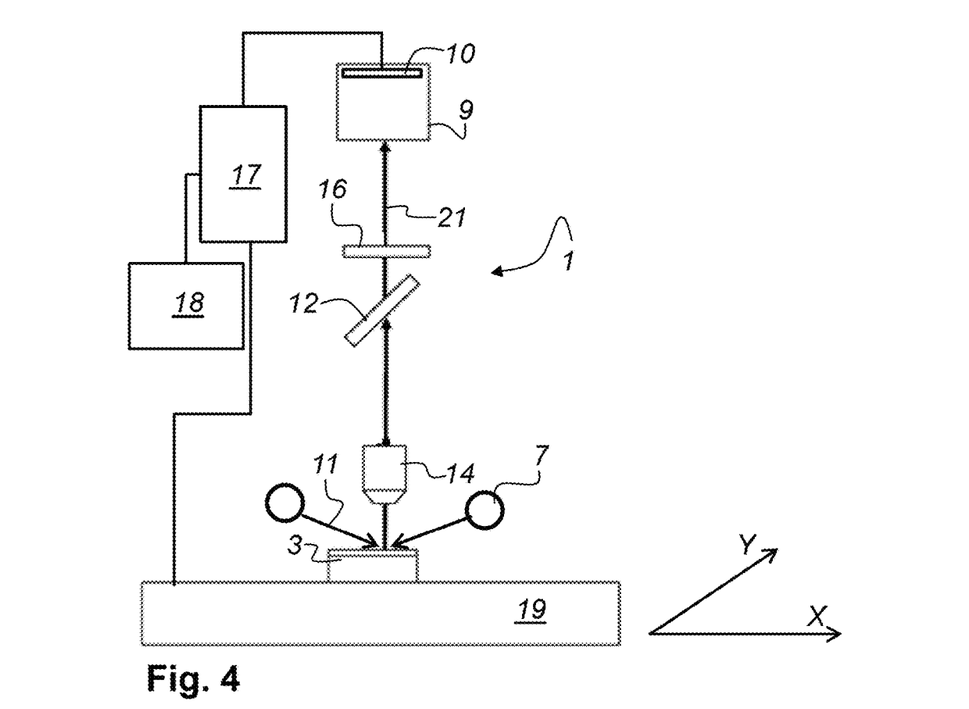
FIG. 4 is an embodiment of an apparatus according to the invention for illuminating one or several LED die/chips and detecting emitted light from the one or several LED die/chips.

FIG. 4 illustrates a further embodiment of the apparatus 1 for illuminating one or several LED die/chips 5 on a substrate 3 to detect the wavelengths of the emitted light from the LED die/chips 5. In the embodiment shown, the LED die/chips 5 are illuminated with a light source 7 configured as a ring light source. The ring light source comprises several LEDs which emit wavelengths able to generate electron-hole pairs in the LED die/chips 5 on a substrate 3. The light emitted by the LED die/chips 5 (caused by generating the electron-hole pairs and the following recombination process) is captured with a camera 9 sensitive to the wavelengths of the emitted light. The camera 9 has a sensor 10, and the response (gray value) of the sensor 10 is a measure of the power of the light output of the LED die/chips 5 and can, for example, be used to classify the LEDs according to their light output power.

The ring light source defines an illumination beam path 11, which illuminates a certain area on the LED die/chips 5 on a substrate 3. The embodiment shown in FIG. 4 does not need a first filter 15 for the illumination beam path 11 of the surface of the LED die/chips 5. The LEDs of the ring light source are driven in such a way that the required light is emitted to generate the electron-hole pairs in the semiconductor material. The semiconductor material will then emit light at a known wavelength, which is collected by the objective lens 14. The objective lens 14 defines a detection beam path 21.

Figure 5:
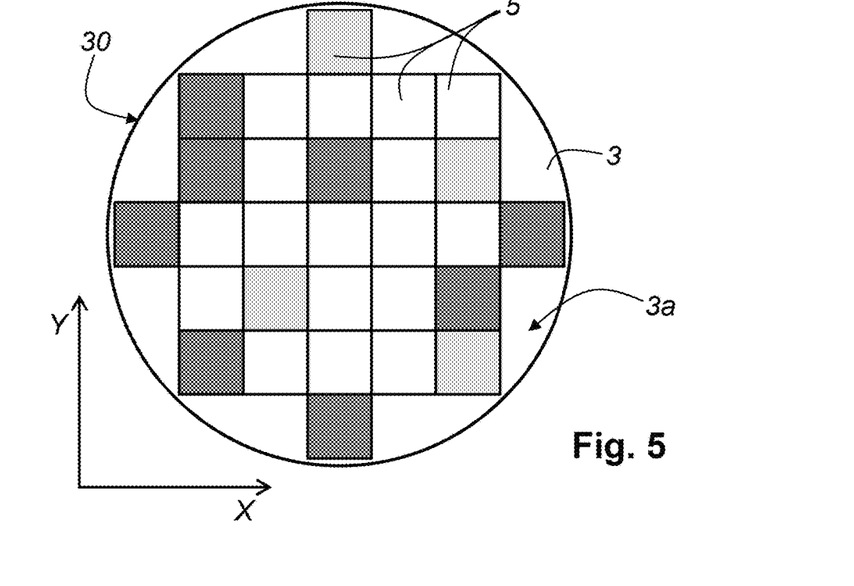
FIG. 5 is a simplified view of a wafermap generated with the inventive apparatus.

FIG. 5 is a simplified view of a wafermap 30 generated with the inventive apparatus 1. The X/Y-stage 19 moves, allowing an entire image of a surface 3a of the substrate 3 (wafer) to be obtained. The computer system 17 stitches individual images, taken with the objective lens 14, together to obtain a representation of the entire surface 3a of the substrate 3 (wafer). In the case of the layer stack 101 of an LED, as shown in FIG. 2, the intermediate layer 103 of InGaN MQW is visible with the inventive apparatus 1. Additionally, the intermediate layer 103 of InGaN MQW is visible below the top layer 104 of p-type GaN. The computer system 17 computes the wafermap 30, plotting the results of all LEDs on their coordinate position on the substrate 3 (wafer). The representation may use different gray scales. An image of the surface 3a of the substrate 3 (wafer) is taken during inspection with an inserted first filter 15 and second filter 16. A spot size (not shown) of the illumination light may be larger than the size of the LED die/chips 5. Thus, it is possible to illuminate the whole LED, resulting in a measurement that is a correct representation of the characteristics of the whole LED die/chips 5. A calibration is performed to correlate the measured average intensity of the LED material to an output power (density) number.

Figure 6A:
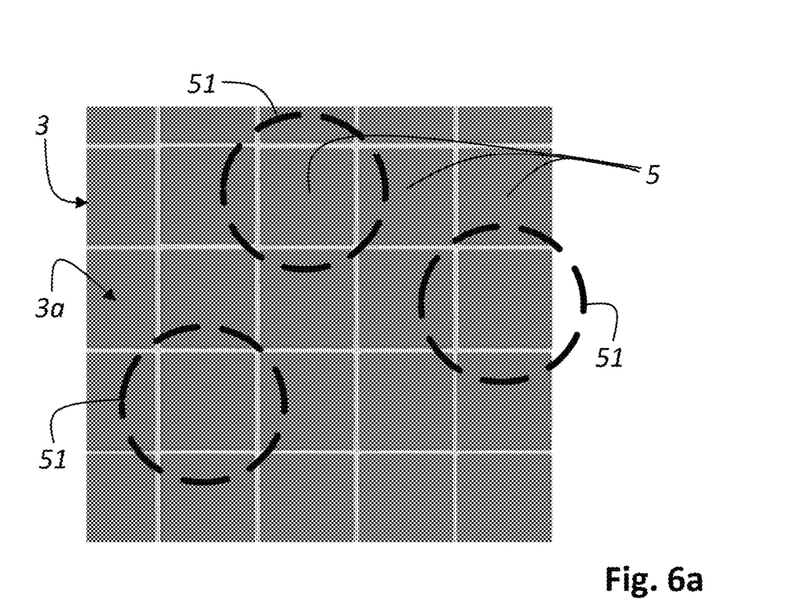
FIG. 6a is an image of a surface of a wafer with LED die/chips illuminated with normal illumination.
Figure 6B:
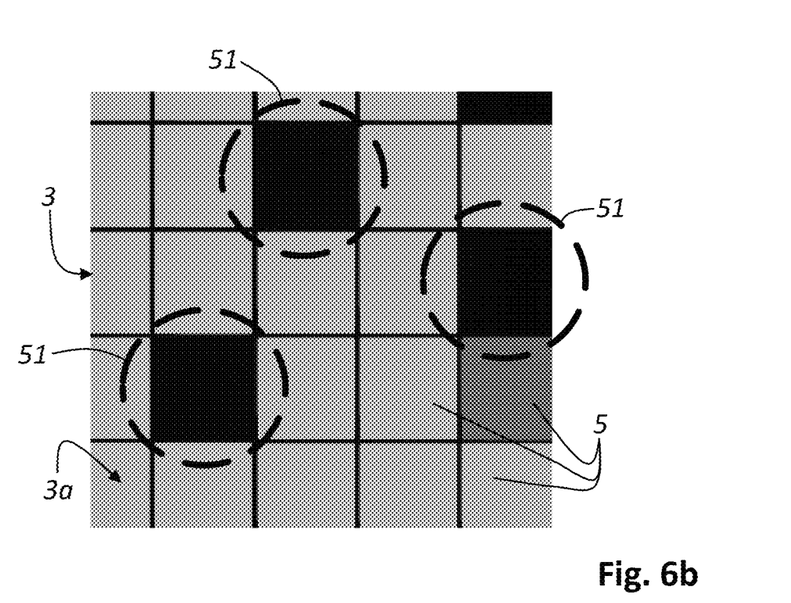
FIG. 6b is an image of an InGaN—layer below a surface of LED die/chips on a wafer illuminated with photoluminescence illumination.

FIG. 6a is an image of the surface 3a of a substrate 3 (wafer) with the LED die/chips 5 illuminated with normal illumination (white light). The image of the surface 3a of a substrate 3 (wafer) with the LED die/chips 5 is taken using standard illumination. With this illumination, all LED die/chips 5 appear to be identical. FIG. 6b is an image of the surface 3a of a substrate 3 (wafer) with the LED die/chips 5, wherein the surface 3a is illuminated with the first filter 15 in the illumination beam path 11 and the image is captured via the second filter 16 in the detection beam path 21. Due to the photoluminescence, the surface 3a of a substrate 3 (wafer) shines in blue light generated by the LED die/chips 5. It is clear from the comparison of FIG. 6a and FIG. 6b that with the photoluminescence setup, inspection features become visible that are invisible with the "normal" or standard illumination setup (white light). The intermediate layer 103 of InGaN MQW is clearly visible below the surface or the top layer 104 of p-type GaN. Circles 51 (shown with dashed lines) indicate LED die/chips 5 with identical appearance under normal illumination (white light), but without response under the photoluminescence setup. All LED die/chips 5 have the same gray scale value (GV) when using the standard illumination setup (white light), but the LED die/chips 5 can have a significantly different GV response when using the photoluminescence setup.

Figure 7:
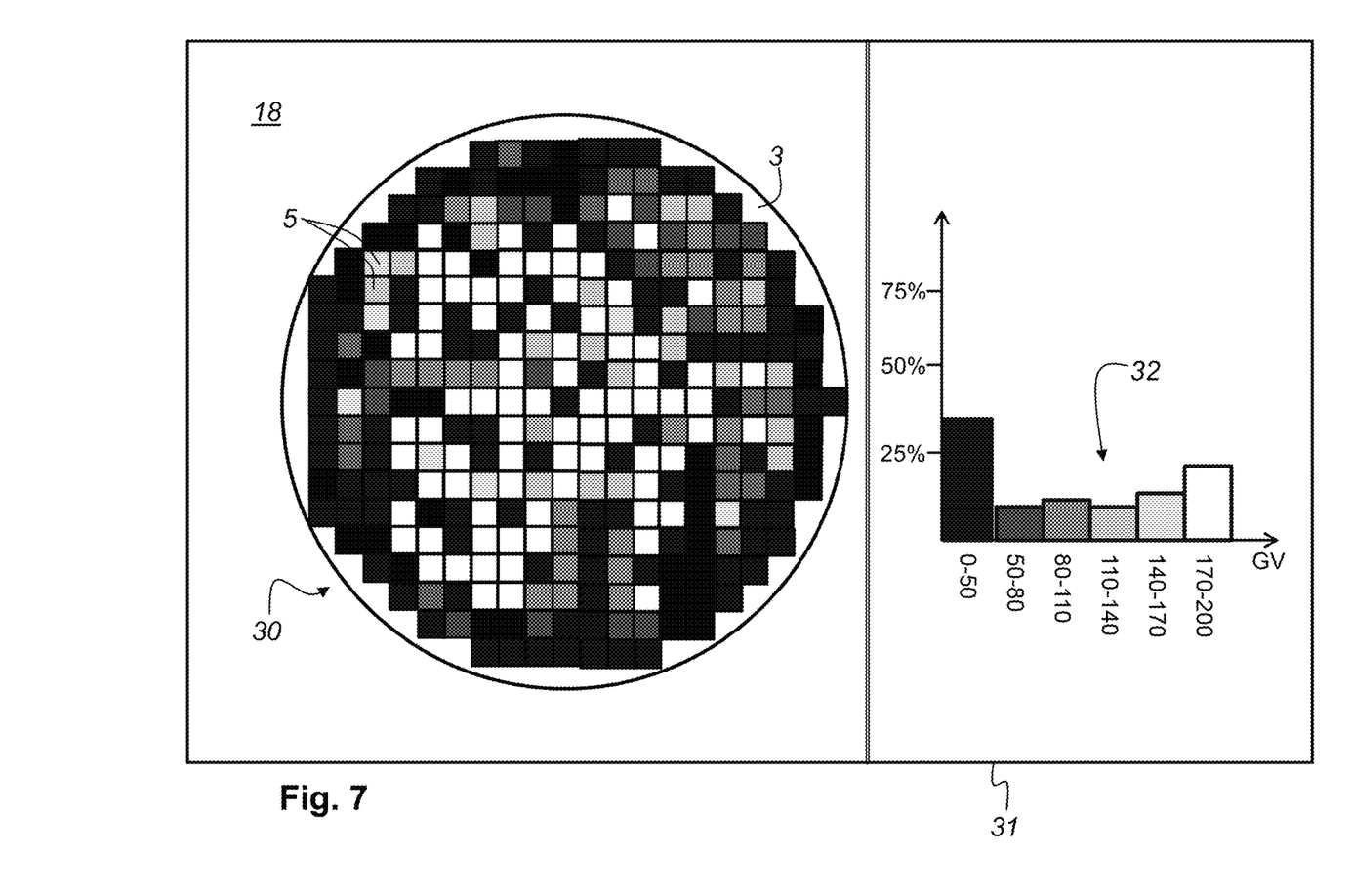
FIG. 7 is a schematic image of a wafermap showing an image of LED die/chips in a photoluminescence setup.

FIG. 7 is a screenshot of the wafermap 30 showing an image of the LED die/chips 5 in the photoluminescence setup on the display 18. Using software implemented in the computer system 17 (see FIG. 3 or 4), an inspection of the properties of LEDs or LED die/chips 5 images is possible. Thus, it is possible to locate the individual LED die/chips 5 on the images, measure certain properties based on image processing, and correlate the measurement results to each individual LED die/chip 5. A recipe is set up with rule-based binning ("RBB"), where a classification of the LED die/chips 5 according to the average GV of the entire LED die/chip 5 on the substrate 3 is carried out. Each class has a separate color code. In a separate section 31 of the display 18, the various GVs are shown in a histogram 32 resulting from the rule-based binning. The inspection of the substrate 3 (wafer) with the LED die/chips 5 shows a signature, making it possible with the photoluminescence setup to measure something genuinely different from what can be seen with normal inspection setup. It can also be seen that the response of individual LED die/chips 5, which can be neighboring, can be independent of the wafer-level signature. This is a clear indication that measurement on the die level is an additional source of information in the process improvement of LED manufacturing. With the wafermap 30, it can be shown that with a measurement on a partly or fully processed substrate 3 (wafer) with LEDs taken, using a photoluminescence setup, a quantitative indication of the expected output power for each individual LED is obtained.

The inventive method is suitable for inspecting at least one LED die/chip 5, or more generally a light emitting semiconductor material, which is structured on a substrate 3 or wafer. The area of at least one LED die/chip 5 is illuminated with a waveband ($\lambda_A \pm \lambda_B$) able to generate electron-hole pairs in the LED die/chip 5 to be inspected. The waveband is obtained via the first filter 15 in the illumination beam path 11. At least a part of the light emitted by the LED die/chip 5 is captured with the sensor 10 of the camera 9. The second filter 16 is positionable to make sure only the light emitted by the LED die/chips 5 on the substrate 3 reaches the camera 9 and the sensor 10. Sensor 10 is sensitive to wavelengths ($\lambda_C \pm \lambda_D$) of the emitted light, and the wavelength $\lambda_C$ is larger than the wavelengths ($\lambda_A + \lambda_B$). The inspection result is the output of the sensor 10, which is fed to the computer system 17.

The inspection result is a measure of the light output power of an LED or a LED die/chip 5. The output of the sensor 10 is at least one gray value of at least one pixel. Usually, the gray value is represented by a matrix of pixels. The range of the gray value, e.g. for an 8 bit computer system 17 is between 0-255 per LED die/chip 5. The output power is a function of the measured gray values. The function can be implemented as a look up table or as a polynomial. The calibration of the look up table or the polynomial is done by measuring light output power of a LED sample when connected to an electrical prober.

The inspection result is at least one gray value per LED die/chip 5, and the LEDs are sorted in at least two bins according to their gray value (at least one threshold value).

In this case, the inspection result includes at least two gray values per LED die/chip 5. The variations/differences in gray value of one LED die/chip 5 are used as a quality measure of the LED die/chip 5.

The inspection result includes at least one gray value per LED die/chip 5 of each LED die/chip 5 multiple inspection image (at least two are taken to detect emitted light stability and deviations). All images can be taken under the same conditions, or images can be taken under varying illumination intensity and/or exposure settings, where the first inspection image is taken under condition A, the second under condition B, where conditions A, B, and so on are configurable. Calibration of parameters may be done using the result from an electrical prober. A histogram of the gray values is generated for each LED die/chip 5 and a classification, under a pass or fail criteria, is done by analyzing the histogram distribution. Examples of classification under a pass of fail criteria include: If the histogram distribution is bi-modal, then fail; If the histogram distribution is uni-modal and has a low gray value, then fail; If the histogram distribution is uni-modal and has a high gray value, then pass. One of the methods above can be used as pre/post check for the electrical prober calibration.

The invention has been described with reference to specific embodiments. It is obvious to a person skilled in the art, however, that alterations and modifications can be made without leaving the scope of the subsequent claims.

What is claimed is:

1. An apparatus for inspection of light emitting semiconductor devices on a substrate, comprising:
   a broadband light source configured to simultaneously illuminate two or more light emitting semiconductor devices of the substrate at one or more points in a semiconductor production process, wherein at least some of the light emitting semiconductor devices, in response to the illumination from the broadband source, emit at least some light caused by a recombination process of electron-hole pairs in an active layer of the light emitting semiconductor devices;
   an objective lens defining a detection beam path;
   a camera with a sensor positioned in the detection beam path for receiving light from the light emitting semiconductor devices via the objective lens, wherein the sensor registers gray scale values for the two more light emitting semiconductor devices;
   a first filter disposed within in an illumination beam path of the broadband light source, wherein the first filter is configured to pass a waveband $\lambda_A + \lambda_B$;
   a second filter disposed within the detection path, wherein the second filter is configured to block reflected incident light from reaching the sensor, wherein the second filter is further configured to pass light emitted by one or more of the light emitting semiconductor devices of at least a wavelength of $\lambda_C$; and
   a computer system communicatively coupled to the sensor, wherein the computer system is configured to determine one or more characteristics of the semiconductor production process based on the light of wavelength $\lambda_C$.

2. The apparatus of claim 1, wherein the light source is a ring light source.

3. The apparatus of claim 2, wherein the ring light source has a plurality of LEDs.

4. The apparatus of claim 1, wherein the light source is a coaxial light source.

5. The apparatus of claim 1, wherein the light source is at least one of a pulsed light source or a continuous light source.

6. The apparatus of claim 1, wherein a waveband constraint $(\lambda_A + \lambda_B) < \lambda_C$ is implemented with the first filter and the second filter.

7. The apparatus of claim 1, further comprising:
   a stage movable in the X/Y-directions, wherein the computer system controls movement of the stage so an entire surface of the light emitting semiconductor devices on the substrate is imaged via the objective lens in the sensor of the camera.

8. The apparatus of claim 1, wherein the two or more light emitting semiconductor devices comprise:
   two or more LED die, wherein light emitted from the two or more LED is caused by a recombination process of electron hole pairs that are generated by the illumination in an active layer of the LED die.

9. An apparatus for inspection of light emitting semiconductor devices on a substrate comprises:
   a ring light source configured to simultaneously illuminate two or more LED die of the substrate at one or more points in a semiconductor production process, wherein at least some of the light emitting semiconductor devices, in response to the illumination from the ring light source, emit at least some light caused by a recombination process of electron-hole pairs in an active layer of the LED devices;
   an objective lens defining a detection beam path;
   a camera with a sensor positioned in the detection beam path for receiving light from the LEDs via the objective lens;
   a first filter disposed within in an illumination beam path of the broadband light source wherein the first filter is configured to pass a waveband $\lambda_A + \lambda_B$;
   a second filter disposed within the detection path, wherein the second filter is configured to block reflected incident light from reaching the sensor, wherein the second filter is further configured to pass light emitted by one or more of the LEDs of at least a wavelength of $\lambda_C$; and
   a computer system communicatively coupled to the sensor, wherein the computer system is configured to determine one or more characteristics of the semiconductor production process based on the light of wavelength $\lambda_C$.

10. An apparatus for inspection of light emitting semiconductor devices on a substrate, comprising:
    a coaxial light source configured to simultaneously illuminate two or more LED die of the substrate at one or more points in a semiconductor production process, wherein at least some of the light emitting semiconductor devices, in response to the illumination from the coaxial light source, emit at least some light caused by a recombination process of electron-hole pairs in an active layer of the LED devices;
    an objective lens defining an illumination beam path
    a first filter disposed within in the illumination beam path of the broadband light source wherein the first filter is configured to pass a waveband $\lambda_A + \lambda_B$;
    a camera with a sensor positioned in a detection beam path for receiving light from the LEDs via the objective lens and a second filter, wherein the sensor registers gray scale values of the two more LED die, wherein the second filter is configured to block reflected incident light from reaching the sensor, wherein the second filter is further configured to pass light emitted by one or more of the LEDs of at least a wavelength of $\lambda_C$; and a computer communicatively coupled to the sensor, wherein the computer system is configured to determine one or more characteristics of the semiconductor production process based on the light of wavelength $\lambda_C$.

11. The apparatus of claim 1, wherein the computer system is further configured to determine one or more characteristics of the semiconductor production process by comparing the intensity of light of wavelength $\lambda_C$ at a first point in the semiconductor production process to the intensity of light of wavelength $\lambda_C$ at an additional point in the semiconductor production process.

12. The apparatus of claim 1, wherein the computer system is further configured to determine an efficiency of at least some of the two or more light emitting semiconductor devices based on the intensity of light of wavelength $\lambda_C$.

13. The apparatus of claim 1, wherein the computer system is further configured to identify a defective light emitting semiconductor device based on the identification of one or more black regions on the light emitting semiconductor device.

* * * * *